United States Patent
Wypych

(10) Patent No.: US 11,399,939 B2
(45) Date of Patent: *Aug. 2, 2022

(54) METHODS AND DEVICES FOR REDUCING PARAVALVULAR LEAKAGE

(71) Applicant: Cardiac Dimensions Pty. Ltd., Kirkland, WA (US)

(72) Inventor: Rick Wypych, Bellevue, WA (US)

(73) Assignee: Cardiac Dimensions Pty. Ltd., Kirkland, WA (US)

(*) Notice: Subject to any disclaimer, the term of this patent is extended or adjusted under 35 U.S.C. 154(b) by 307 days.

This patent is subject to a terminal disclaimer.

(21) Appl. No.: 16/540,699

(22) Filed: Aug. 14, 2019

(65) Prior Publication Data
US 2019/0365537 A1 Dec. 5, 2019

Related U.S. Application Data

(63) Continuation of application No. 15/453,734, filed on Mar. 8, 2017, now Pat. No. 10,390,953.

(51) Int. Cl.
*A61F 2/24* (2006.01)

(52) U.S. Cl.
CPC .......... *A61F 2/2451* (2013.01); *A61F 2/2412* (2013.01); *A61F 2/2466* (2013.01); *A61F 2220/0008* (2013.01)

(58) Field of Classification Search
CPC ........ A61F 2/24; A61F 2/2409; A61F 2/2427; A61F 2/2442; A61F 2/2445; A61F 2/2451; A61F 2/246
See application file for complete search history.

(56) References Cited

U.S. PATENT DOCUMENTS

| | | |
|---|---|---|
| 3,620,212 A | 11/1971 | Fannon, Jr. et al. |
| 3,786,806 A | 1/1974 | Johnson et al. |
| 3,890,977 A | 6/1975 | Wilson |
| 3,974,526 A | 8/1976 | Dardik et al. |

(Continued)

FOREIGN PATENT DOCUMENTS

| | | |
|---|---|---|
| EP | 0893133 A1 | 1/1999 |
| EP | 0903110 A1 | 3/1999 |

(Continued)

OTHER PUBLICATIONS

Halees; An additional maneuver to repair mitral paravalvular leak; European Journal of Cardio-Thoracic Surgery; 39(3); pp. 410-411 ; Mar. 2011 (Year: 2011).*

*Primary Examiner* — Todd J Scherbel
(74) *Attorney, Agent, or Firm* — Shay Glenn LLP; Thomas M. Zlogar

(57) ABSTRACT

Methods and devices for reducing paravalvular leakage associated with a replacement mitral valve. The methods can include monitoring for paravalvular leakage between a replacement mitral valve and tissue proximate the mitral valve annulus; if a sufficient amount of paravalvular leakage is observed, deploying a tissue reshaping device at least partially within a coronary sinus; remodeling coronary sinus tissue with the tissue reshaping device to remodel at least one of mitral valve annulus tissue, at least one mitral valve leaflet, and left atrium tissue in an attempt to reduce the paravalvular leakage; and monitoring for a reduction in paravalvular leakage after the remodeling step.

18 Claims, 2 Drawing Sheets

(56) References Cited

U.S. PATENT DOCUMENTS

| | | |
|---|---|---|
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,099,838 A | 3/1992 | Bardy |
| 5,104,404 A | 4/1992 | Wolff |
| 5,197,978 A | 3/1993 | Hess |
| 5,250,071 A | 10/1993 | Palermo |
| 5,261,916 A | 11/1993 | Engelson |
| 5,265,601 A | 11/1993 | Mehra |
| 5,344,426 A | 9/1994 | Lau et al. |
| 5,350,420 A | 9/1994 | Cosgrove et al. |
| 5,411,549 A | 5/1995 | Peters |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,617,854 A | 4/1997 | Munsif |
| 5,662,703 A | 9/1997 | Yurek et al. |
| 5,676,671 A | 10/1997 | Inoue |
| 5,733,325 A | 3/1998 | Robinson et al. |
| 5,733,328 A | 3/1998 | Fordenbacher |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,001,118 A | 12/1999 | Daniel et al. |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,045,497 A | 4/2000 | Schweich, Jr. et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,159,220 A | 12/2000 | Gobron et al. |
| 6,162,168 A | 12/2000 | Schweich, Jr. et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,306,141 B1 | 10/2001 | Jervis |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,368,345 B1 | 4/2002 | Dehdashtian et al. |
| 6,395,017 B1 | 5/2002 | Dwyer et al. |
| 6,402,781 B1 | 6/2002 | Langberg et al. |
| 6,409,750 B1 | 6/2002 | Hyodoh et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,478,776 B1 | 11/2002 | Rosenman et al. |
| 6,503,271 B2 | 1/2003 | Duerig et al. |
| 6,537,314 B2 | 3/2003 | Langberg et al. |
| 6,556,873 B1 | 4/2003 | Smits |
| 6,562,066 B1 | 5/2003 | Martin |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,652,571 B1 | 11/2003 | White et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Holland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,798,231 B2 | 9/2004 | Iwasaki et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,827,690 B2 | 12/2004 | Bardy |
| 6,881,220 B2 | 4/2005 | Edwin et al. |
| 6,890,353 B2 | 5/2005 | Cohn et al. |
| 6,899,734 B2 | 5/2005 | Castro et al. |
| 6,908,478 B2 | 6/2005 | Alferness et al. |
| 6,908,482 B2 | 6/2005 | McCarthy et al. |
| 6,926,690 B2 | 8/2005 | Renati |
| 6,935,404 B2 | 8/2005 | Duerig et al. |
| 6,949,122 B2 | 9/2005 | Adams et al. |
| 6,955,689 B2 | 10/2005 | Ryan et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 7,004,958 B2 | 2/2006 | Adams et al. |
| 7,087,064 B1 | 8/2006 | Hyde |
| 7,128,073 B1 | 10/2006 | van der Burg et al. |
| 7,152,605 B2 | 12/2006 | Khairkhahan et al. |

(56) References Cited

U.S. PATENT DOCUMENTS

| | | |
|---|---|---|
| 7,175,653 B2 | 2/2007 | Gaber |
| 7,179,282 B2 | 2/2007 | Alferness et al. |
| 7,270,676 B2 | 9/2007 | Alferness et al. |
| 7,276,078 B2 | 10/2007 | Spenser et al. |
| 7,309,354 B2 | 12/2007 | Mathis et al. |
| 7,311,729 B2 | 12/2007 | Mathis et al. |
| 7,316,708 B2 | 1/2008 | Gordon et al. |
| 7,364,588 B2 | 4/2008 | Mathis et al. |
| 7,452,375 B2 | 11/2008 | Mathis et al. |
| 7,503,931 B2 | 3/2009 | Kowalsky et al. |
| 7,591,826 B2 | 9/2009 | Alferness et al. |
| 7,608,102 B2 | 10/2009 | Adams et al. |
| 7,635,387 B2 | 12/2009 | Reuter et al. |
| 7,637,946 B2 | 12/2009 | Solem et al. |
| 7,674,287 B2 | 3/2010 | Alferness et al. |
| 7,758,639 B2 | 7/2010 | Mathis |
| 7,814,635 B2 | 10/2010 | Gordon et al. |
| 7,828,841 B2 | 11/2010 | Mathis et al. |
| 7,828,842 B2 | 11/2010 | Nieminen et al. |
| 7,828,843 B2 | 11/2010 | Alferness et al. |
| 7,837,728 B2 | 11/2010 | Nieminen et al. |
| 7,837,729 B2 | 11/2010 | Gordon et al. |
| 7,887,582 B2 | 2/2011 | Mathis et al. |
| 7,955,384 B2 | 6/2011 | Rafiee et al. |
| 8,006,594 B2 | 8/2011 | Hayner et al. |
| 8,062,358 B2 | 11/2011 | Mathis et al. |
| 8,075,608 B2 | 12/2011 | Gordon et al. |
| 8,172,898 B2 | 5/2012 | Alferness et al. |
| 8,182,529 B2 | 5/2012 | Gordon et al. |
| 8,250,960 B2 | 8/2012 | Hayner et al. |
| 8,439,971 B2 | 5/2013 | Reuter et al. |
| 8,795,356 B2 | 8/2014 | Quadri et al. |
| 8,974,525 B2 | 3/2015 | Nieminen et al. |
| 9,039,757 B2 | 5/2015 | McLean et al. |
| 9,084,676 B2 | 7/2015 | Chau et al. |
| 9,320,600 B2 | 4/2016 | Nieminen et al. |
| 9,370,418 B2 | 6/2016 | Pintor et al. |
| 9,408,695 B2 | 8/2016 | Mathis et al. |
| 9,474,608 B2 | 10/2016 | Mathis et al. |
| 9,526,616 B2 | 12/2016 | Nieminen et al. |
| 9,597,186 B2 | 3/2017 | Nieminen et al. |
| 9,827,098 B2 | 11/2017 | Mathis et al. |
| 9,827,099 B2 | 11/2017 | Mathis et al. |
| 9,827,100 B2 | 11/2017 | Mathis et al. |
| 9,956,076 B2 | 5/2018 | Mathis et al. |
| 9,956,077 B2 | 5/2018 | Nieminen et al. |
| 10,052,205 B2 | 8/2018 | Mathis et al. |
| 10,166,102 B2 | 1/2019 | Nieminen et al. |
| 10,327,900 B2 | 6/2019 | Mathis et al. |
| 10,390,953 B2 * | 8/2019 | Wypych ............... A61F 2/2451 |
| 10,449,048 B2 | 10/2019 | Nieminen et al. |
| 10,456,257 B2 | 10/2019 | Mathis et al. |
| 10,456,259 B2 | 10/2019 | Mathis et al. |
| 11,109,971 B2 | 9/2021 | Nieminen et al. |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0010507 A1 | 1/2002 | Ehr et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0161393 A1 | 10/2002 | Demond et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0193827 A1 | 12/2002 | McGuckin et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0093148 A1 | 5/2003 | Bolling et al. |
| 2003/0130730 A1 | 7/2003 | Cohn et al. |
| 2003/0135267 A1 | 7/2003 | Solem et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0172046 A1 | 9/2004 | Hlavka et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0260342 A1 | 12/2004 | Vargas et al. |
| 2004/0260384 A1 | 12/2004 | Allen |
| 2005/0004667 A1 | 1/2005 | Swinford et al. |
| 2005/0027351 A1 | 2/2005 | Reuter et al. |
| 2005/0033419 A1 | 2/2005 | Alferness et al. |
| 2005/0060030 A1 | 3/2005 | Lashinski et al. |
| 2005/0085903 A1 | 4/2005 | Lau |
| 2005/0096740 A1 | 5/2005 | Langberg et al. |
| 2005/0107810 A1 | 5/2005 | Morales et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0149182 A1 | 7/2005 | Alferness et al. |
| 2005/0177228 A1 | 8/2005 | Solem et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0222678 A1 | 10/2005 | Lashinski et al. |
| 2005/0261704 A1 | 11/2005 | Mathis |
| 2005/0272969 A1 | 12/2005 | Alferness et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0271174 A1 | 11/2006 | Nieminen et al. |
| 2007/0027533 A1 | 2/2007 | Douk |
| 2007/0066879 A1 | 3/2007 | Mathis et al. |
| 2007/0073391 A1 | 3/2007 | Bourang et al. |
| 2007/0173926 A1 | 7/2007 | Bobo, Jr. et al. |
| 2007/0239270 A1 | 10/2007 | Mathis et al. |
| 2008/0015407 A1 | 1/2008 | Mathis et al. |
| 2008/0015679 A1 | 1/2008 | Mathis et al. |
| 2008/0015680 A1 | 1/2008 | Mathis et al. |
| 2008/0071364 A1 | 3/2008 | Kaye et al. |
| 2008/0221673 A1 | 9/2008 | Bobo et al. |
| 2010/0030330 A1 | 2/2010 | Bobo et al. |
| 2010/0280602 A1 | 11/2010 | Mathis |
| 2011/0066234 A1 | 3/2011 | Gordon et al. |
| 2011/0106117 A1 | 5/2011 | Mathis et al. |
| 2012/0123532 A1 | 5/2012 | Mathis |
| 2012/0197389 A1 | 8/2012 | Alferness et al. |

(56) References Cited

U.S. PATENT DOCUMENTS

| | | |
|---|---|---|
| 2014/0275757 A1 | 9/2014 | Goodwin et al. |
| 2017/0165058 A1 | 6/2017 | Rothstein et al. |
| 2017/0189185 A1 | 7/2017 | Nieminen et al. |
| 2018/0078365 A1 | 3/2018 | Zhang et al. |
| 2018/0256330 A1 | 9/2018 | Wypych |
| 2019/0262136 A1 | 8/2019 | Nieminen et al. |
| 2020/0008943 A1 | 1/2020 | Mathis et al. |
| 2020/0253732 A1 | 8/2020 | Nieminen et al. |
| 2021/0298732 A1 | 9/2021 | Nieminen et al. |
| 2021/0330460 A1 | 10/2021 | Mathis et al. |
| 2021/0393403 A1 | 12/2021 | Nieminen et al. |

FOREIGN PATENT DOCUMENTS

| | | |
|---|---|---|
| EP | 0968688 A1 | 1/2000 |
| EP | 1050274 A1 | 11/2000 |
| EP | 1095634 A2 | 5/2001 |
| EP | 1177779 A2 | 2/2002 |
| EP | 2181670 A2 | 5/2010 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| SE | 9902455 | 12/2000 |
| WO | WO98/56435 A1 | 12/1998 |
| WO | WO00/44313 A1 | 8/2000 |
| WO | WO00/60995 A2 | 10/2000 |
| WO | WO00/74603 A1 | 12/2000 |
| WO | WO01/00111 A1 | 1/2001 |
| WO | WO01/19292 A1 | 3/2001 |
| WO | WO01/50985 A1 | 7/2001 |
| WO | WO01/54618 A1 | 8/2001 |
| WO | WO01/87180 A2 | 11/2001 |
| WO | WO02/00099 A2 | 1/2002 |
| WO | WO02/01999 A2 | 1/2002 |
| WO | WO02/05888 A1 | 1/2002 |
| WO | WO02/19951 A1 | 3/2002 |
| WO | WO02/34118 A2 | 5/2002 |
| WO | WO02/47539 A2 | 6/2002 |
| WO | WO02/053206 A2 | 7/2002 |
| WO | WO02/060352 A1 | 8/2002 |
| WO | WO02/062263 A2 | 8/2002 |
| WO | WO02/062270 A1 | 8/2002 |
| WO | WO02/062408 A2 | 8/2002 |
| WO | WO02/076284 A2 | 10/2002 |
| WO | WO02/078576 A2 | 10/2002 |
| WO | WO02/096275 A2 | 12/2002 |
| WO | WO03/015611 A2 | 2/2003 |
| WO | WO03/037171 A2 | 5/2003 |
| WO | WO03/049647 A1 | 6/2003 |
| WO | WO03/049648 A2 | 6/2003 |
| WO | WO03/055417 A1 | 7/2003 |
| WO | WO03/059198 A2 | 7/2003 |
| WO | WO03/063735 A2 | 8/2003 |
| WO | WO2004/045463 A2 | 6/2004 |
| WO | WO2004/084746 A2 | 10/2004 |
| WO | WO2005/046531 A2 | 5/2005 |
| WO | WO2005/058206 A1 | 6/2005 |
| WO | WO2006/002492 A1 | 1/2006 |

\* cited by examiner

METHODS AND DEVICES FOR REDUCING PARAVALVULAR LEAKAGE

CROSS REFERENCE TO RELATED APPLICATIONS

This application is a continuation of U.S. application Ser. No. 15/453,734, filed Mar. 8, 2017, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Paravalvular leak is a complication associated with the implantation of a prosthetic heart valve (e.g., a replacement mitral valve), whether implanted surgically or with a transcatheter approach. Paravalvular leak refers to blood flowing through a channel or space between the implanted valve and cardiac tissue as a result of a lack of appropriate sealing. Paravalvular leaks are generally considered more common with replacement mitral valves than with replacement aortic valves. Some leaks may be characterized as small, non-significant leaks, but larger leaks can lead to heart failure and increased risk of infectious endocarditis. Significant leaks are currently treated either surgically or using the transcatheter deployment of occlusion devices, such as plugs. Existing techniques can be complicated because the follow up corrective procedure manipulates tissue adjacent the replacement valve, which can cause disruption or dislodgement of the replacement valve. Alternative methods and devices for minimizing or reducing paravalvular leakage associated with the implantation of a replacement heart valve are therefore needed.

SUMMARY OF THE DISCLOSURE

Some embodiments are methods of reducing paravalvular leakage associated with a replacement mitral valve, comprising: monitoring for paravalvular leakage between a replacement mitral valve and tissue proximate the mitral valve annulus; if a sufficient amount of paravalvular leakage is observed, deploying a tissue reshaping device at least partially within a coronary sinus; remodeling coronary sinus tissue with the tissue reshaping device to remodel at least one of mitral valve annulus tissue, at least one mitral valve leaflet, and left atrium tissue in an attempt to reduce the paravalvular leakage; and monitoring for a reduction in paravalvular leakage after the remodeling step.

After monitoring for a reduction in paravalvular leakage after the remodeling step, if the monitored paravalvular leakage has been sufficiently reduced, the methods can include maintaining the remodeling of the coronary sinus with the tissue reshaping device and maintaining the remodeling of the at least one of the mitral valve annulus tissue, mitral valve leaflets, and left atrium tissue to maintain the reduced paravalvular leakage. The maintaining step can comprise releasing the tissue reshaping device from a delivery device to implant the tissue reshaping device. The method can further comprise releasing the replacement mitral valve from a delivery device.

The methods can further comprise, if the monitored paravalvular leakage has been sufficiently reduced, releasing the tissue reshaping device from a delivery device.

The methods can further comprise, if the monitored paravalvular leakage has been sufficiently reduced, releasing the replacement mitral valve from a delivery device. The methods can further comprise monitoring paravalvular leakage after releasing the replacement mitral valve from the device to determine if paravalvular leakage increased to an undesired amount as a result of releasing the replacement mitral valve from the delivery device, and if so, repeating the remodeling and monitoring steps.

The methods can further comprise, after monitoring for paravalvular leakage after the remodeling step, if the paravalvular leakage has not been reduced by a desired amount, further remodeling coronary sinus tissue with the tissue reshaping device to further remodel at least one of mitral valve annulus tissue, mitral valve leaflets, and left atrium tissue in an attempt to reduce paravalvular leakage, and further monitoring paravalvular leakage. If paravalvular leakage has not been sufficiently reduced, the methods can repeat the further remodeling and further monitoring steps until the paravalvular leakage has been reduced by a desired amount. If the paravalvular leakage has been reduced by a desired amount, the methods can include releasing the tissue reshaping device from a delivery device to thereby implant the tissue reshaping device and maintain the reduced paravalvular leakage. If the paravalvular leakage has been reduced by a desired amount, the methods can include releasing the mitral valve replacement from a delivery device.

Remodeling coronary sinus tissue with the tissue reshaping device can comprise plicating coronary sinus tissue with the tissue reshaping device. Deploying a tissue reshaping device can comprise anchoring a first anchor of the tissue reshaping device within the coronary sinus, and wherein plicating coronary sinus tissue can comprise proximally pulling on the tissue reshaping device after the first anchor is anchored within the coronary sinus. The methods can further comprise anchoring a second anchor of the tissue reshaping device against tissue when the monitored paravalvular leakage has been reduced to a desired amount. Deploying a tissue reshaping device can comprise anchoring first and second anchors, and wherein plicating coronary sinus tissue can comprise proximally pulling on a portion of the tissue reshaping device after the first and second anchors are anchored.

Remodeling coronary sinus tissue with the tissue reshaping device can comprise reducing the curvature of at least a portion of the coronary sinus.

Remodeling coronary sinus tissue with the tissue reshaping device can comprise increasing the curvature of at least a portion of the coronary sinus.

Remodeling coronary sinus tissue with the tissue reshaping device can be at least partially caused by pulling on the tissue reshaping device.

Remodeling coronary sinus tissue with the tissue reshaping device can be at least partially caused by straightening at least a portion of the tissue reshaping device.

Remodeling coronary sinus tissue with the tissue reshaping device can be at least partially caused by increasing the curvature of at least a portion of the tissue reshaping device.

The methods can further comprise, prior to the first monitoring step, expanding the replacement mitral valve into contact with at least one of left atrial tissue, mitral valve annulus tissue, native mitral valve leaflet tissue, and left ventricular tissue. The expanded replacement mitral valve can remain secured to a delivery device when the remodeling step is initiated.

If a certain degree of paravalvular leakage is observed after the first monitoring step, the methods can further comprise delivering the tissue reshaping device to the coronary sinus.

Monitoring for paravalvular leakage between the replacement mitral valve and tissue proximate the mitral valve annulus can comprise monitoring blood flow between the replacement mitral valve and tissue using an imaging modality, such as fluoroscopy.

DETAILED DESCRIPTION

Figure 2:
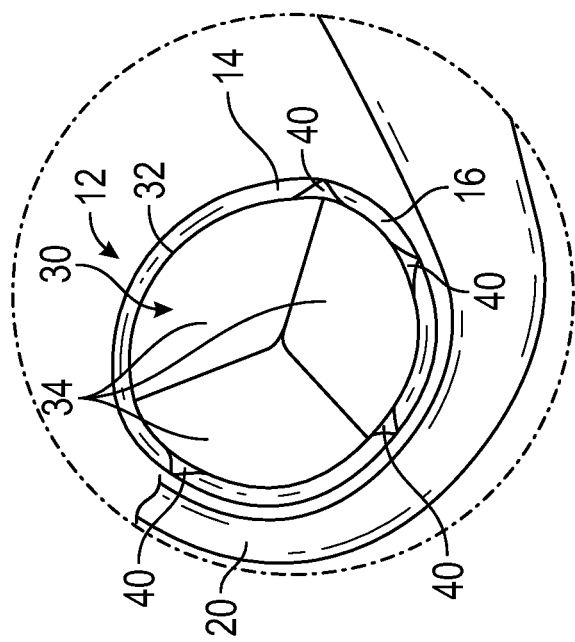
FIG. 2 illustrates exemplary paravalvular leakage occurring after at least partially expanding a replacement mitral valve.

The disclosure herein describes methods and devices for reducing paravalvular leakage associated with a replacement heart valve, and generally a replacement mitral valve. There may, however, be ways in which the methods and devices herein can be utilized to reduce paravalvular leakage associated with other types of replacement heart valves. When used herein, "leakage," or any derivative of "leakage," refers to paravalvular leakage.

The methods herein monitor for paravalvular leakage associated with the deployment of a replacement heart valve. The monitoring may occur during the procedure in which a replacement heart valve is implanted, or it may occur subsequent to the procedure that implants the replacement heart valve. For example, leakage may be monitored subsequent to the procedure if, for example, the patient presents with post-procedure symptoms suggestive of leakage, even if leakage was not observed during the implantation procedure.

The methods herein may be used to reduce any degree of leakage, whether it is considered significant or non-significant leakage.

The methods herein include at least one step to reduce the monitored paravalvular leakage if a sufficient amount of paravalvular leakage has been observed. The amount of leakage that is determined to be significant enough to warrant a subsequent leakage reducing step may depend on a variety of factors, such as a subjective analysis of the physician observing the leakage. When the disclosure herein refers to taking one or more steps to reduce leakage if a sufficient amount of leakage is observed, the disclosure is not indefinite or vague, but merely refers to the fact that some degree of leakage will lead to a decision to carry out a subsequent step to attempt to reduce the leakage. Physicians currently trained to monitor for paravalvular leakage, whether during a replacement valve implantation procedure or otherwise, can make, for example, a subjective assessment about whether a sufficient amount of leakage has been observed. In some instances, the amount of leakage that is determined to be sufficient to warrant intervention may be minimal or non-significant, but in some instances the amount of leakage that is determined to be sufficient to warrant intervention may be considered significant.

Methods herein include, if a sufficient amount of paravalvular leakage is observed, deploying a tissue reshaping device at least partially within a coronary sinus, and remodeling coronary sinus tissue with the tissue reshaping device to remodel at least one of mitral valve annulus tissue, at least one mitral valve leaflet, and left atrium tissue in an attempt to reduce the paravalvular leakage. The methods utilize a device positioned at least partially within the coronary sinus to attempt to reduce leakage. This is partly due to the proximity between a portion of the coronary sinus and the mitral valve annulus. If the method is used for a heart valve other than the mitral valve, the method generally includes deploying a device in proximity to a replacement heart valve, and using the device to remodel annulus tissue or tissue proximate to the native valve annulus.

After remodeling at least one of mitral valve annulus tissue, at least one mitral valve leaflet, and left atrium tissue in an attempt to reduce the paravalvular leakage, the method includes monitoring for a reduction in paravalvular leakage. This monitoring step determines whether any observed leakage has been sufficiently reduced, or if additional steps should be taken to further reduce the leakage. Again, whether any observed leakage has been sufficiently reduced may be determined using a variety of methods, and may be a subjective determination. The specification and claims herein are not indefinite or vague when referring to a sufficient amount of reduction, but are rather describing that there is some amount of reduction that will lead to a determination (automatically or not) that some monitored leakage has been sufficient reduced.

Figure 1:
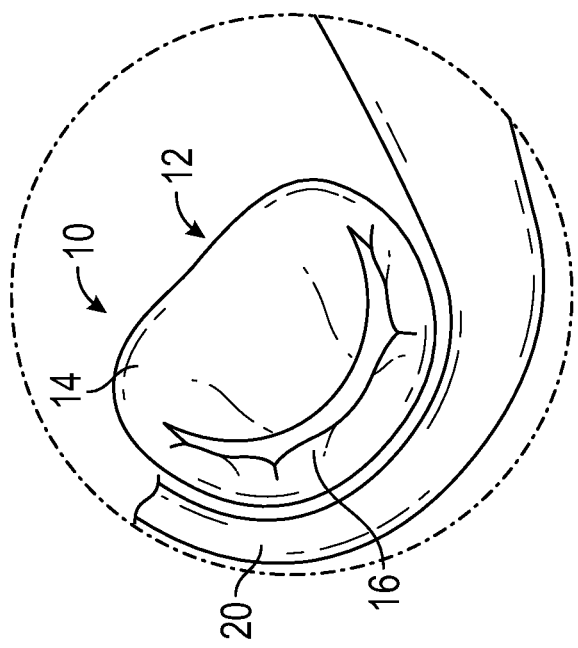
FIG. 1 is a view illustrating the proximity of a coronary sinus and native mitral valve.

FIGS. 1 and 2 illustrate exemplary paravalvular leakage that can occur after implantation of an exemplary replacement mitral valve. FIG. 1 illustrates native mitral valve 10 and coronary sinus 20, which is in proximity to mitral valve 10. Mitral valve 10 includes annulus 12, anterior leaflet 14, and posterior leaflet 16.

FIG. 2 illustrates replacement heart valve 30 in a deployed configuration within the native annulus 20. In this exemplary method the native leaflets 12 and 14 have not been excised, but in other methods the native leaflets may first be excised. Replacement heart valve 30 may be positioned surgically or minimally invasively, using techniques and replacement valves known in the art.

FIG. 2 illustrates replacement heart valve 30 in a fully deployed configuration and positioned within the native mitral valve annulus, but in some embodiments paravalvular leakage can be monitored before the replacement valve is considered to be fully deployed. For example, the methods herein can monitor for leakage when the replacement heart valve is substantially or mostly deployed but before final deployment has occurred (e.g., before release from a delivery system; before expansion of a portion of the replacement heart valve, etc.).

Exemplary replacement valves and methods of delivery and implantation that can be part of methods herein (but without limitation) can be found in the following references, which are incorporated by reference herein: U.S. Pat. Nos. 9,039,757; 8,795,356; 9,084,676; and 9,370,418.

FIG. 2 illustrates observed paravalvular leakage 40 between replacement mitral valve 30 and one more of at least one mitral valve leaflet and the mitral valve annulus. In this example, leakage 40 is shown as a plurality of leakage sites, but the leakage can occur at any location or locations between the replacement valve and native tissue. For example without limitation, the leakage can have one or more of a crescent, oval, or circular configuration, or any other configuration. The leakage 40 may be observed during the procedure that implants replacement valve 30, or it may be observed in a separate monitoring procedure subsequent in time to the implantation procedure.

If the monitoring step occurs during the replacement valve implantation procedure, monitoring for paravalvular leakage may be performed using fluoroscopy, such as with contrast dye, which is known in the art. The physician can look for dye movement between the replacement valve and tissue, indicating paravalvular leakage. If a sufficient amount of leakage is observed, one or more steps can then be taken in an attempt to reduce the leakage, examples of which are provided below.

The monitoring step may occur in a separate procedure subsequent to the replacement heart valve implantation procedure. For example, after the replacement heart valve procedure, a patient may present with symptoms suggestive of paravalvular leakage, and a procedure may be performed to monitor for leakage. Exemplary known techniques that can be used to monitor for paravalvular leakage include, for example, transthoracic echocardiography ("TTE") and transesophageal echocardiography ("TEE"), which produce images of the heart. If a sufficient amount of leakage is observed, one or more steps can then be taken to reduce the leakage, examples of which are provided below.

Figure 3:
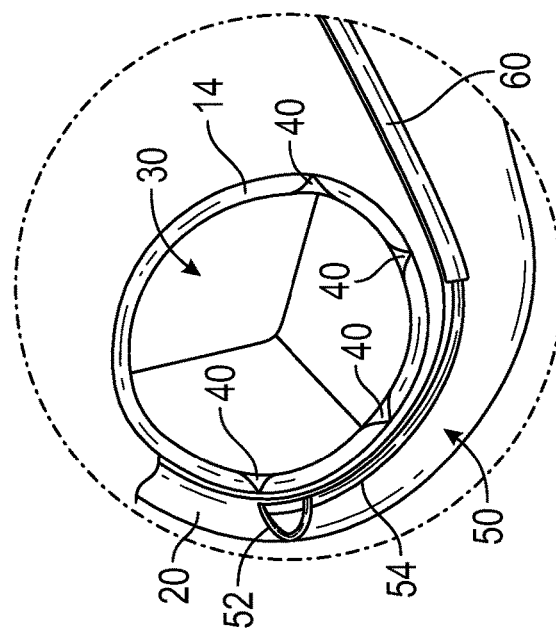
FIG. 3 illustrates the deployment of a first anchor of an exemplary remodeling device in the coronary sinus.
Figure 5:
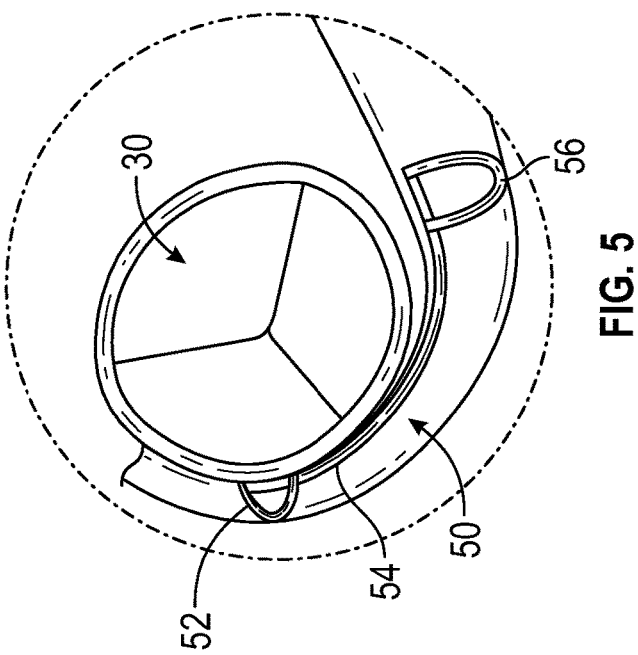
FIG. 5 illustrates a fully deployed exemplary tissue remodeling device, which is maintaining the remodeling of tissue and maintain a reduction in paravalvular leakage.
Figure 4:
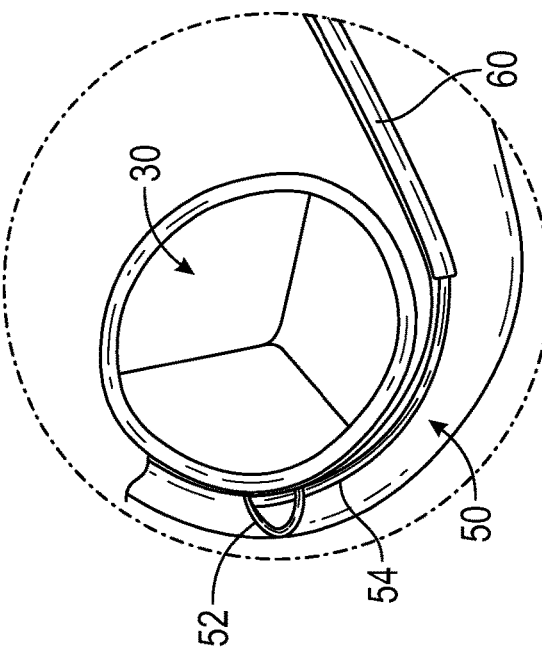
FIG. 4 illustrates remodeling tissue in an attempt to reduce paravalvular leakage between the replacement heart valve and native tissue.

FIGS. 3-5 illustrate a merely exemplary method in which observed paravalvular leakage is reduced. FIGS. 3-5 also illustrate a merely exemplary device that may be used to reduce observed paravalvular leakage. The method in FIGS. 3-5 utilizes the proximity of the coronary sinus and the mitral valve to remodel tissue proximate to the replacement heart valve to reduce paravalvular leakage. In this embodiment, the method includes deploying a tissue reshaping device at least partially within a coronary sinus, and remodeling coronary sinus tissue with the tissue reshaping device to remodel at least one of mitral valve annulus tissue, at least one native leaflet, and left atrium tissue, in an attempt to reduce the paravalvular leakage.

The exemplary method in FIGS. 3-5 includes the use of device 50 that includes first anchor 52 and second anchor 56, and an elongate member 54 extending between the first and second anchors. An example of device 50 that can be used in the method of FIGS. 3-5 is the Carillon® Mitral Contour System®, traditionally used to treat mitral valve regurgitation, but which can be used in this alternative method of reducing paravalvular leakage associated with a replacement mitral heart valve. Device 50 is merely an exemplary device that can be used to reduce leakage, and is shown only by way of example. Other devices can be positioned at least partially within a coronary sinus may be able to reduce leakage by remodeling coronary sinus.

Device 50 is delivered to coronary sinus 20 within delivery device 60 with anchors 52 and 56 in delivery configurations. Depending on when the monitoring step occurs, device 50 can be initially delivered to the coronary sinus at any time before, during or after the implantation of replacement valve 30, including during a subsequent procedure.

After delivery device 60 is positioned in the coronary sinus, it is moved proximally to expose first anchor 52, allowing first anchor 52 to expand, as shown in FIG. 3. An optional locking step may be performed on the distal anchor 52, as is described in the references incorporated herein that describe one or more aspects of the Carillon® device. After first anchor 52 is anchored in place, a tensioning force, generally in the proximal direction, is applied to the proximal end of device 50 by the delivery system, as is shown in FIG. 4. The tensioning force remodels the coronary sinus, as shown in FIG. 4. Because the coronary sinus is in proximity to the mitral valve annulus, remodeling the coronary sinus causes remodeling of at least one of the mitral valve annulus tissue, at least one mitral valve leaflet, and left atrium tissue in an attempt to reduce the paravalvular leakage. Remodeling at least one of mitral valve annulus tissue, at least one mitral valve leaflet, and left atrium tissue remodels the interface between the replacement heart valve 30 and native tissue, creating a more effective seal between the replacement heart valve and native tissue. Creating a more effective seal reduces paravalvular leakage.

After some remodeling has occurred, as shown in FIG. 4, a monitoring step is then performed that monitors for a reduction in paravalvular leakage after the remodeling step. This monitoring step is performed to determine if the remodeling has caused a sufficient reduction in paravalvular leakage. This monitoring step can be performed using a variety of techniques, such as, without limitation, fluoroscopy, TTE, or TEE, or any combination thereof.

If, after this monitoring step, it is determined that paravalvular leakage has been sufficiently reduced (e.g., through a subjective assessment, through an automatic assessment, etc.), the method can then include maintaining the remodeling of the coronary sinus with the tissue reshaping device and maintaining the remodeling of the at least one of the mitral valve annulus tissue, at least one mitral valve leaflet, and left atrium tissue to maintain the reduced paravalvular leakage. In this embodiment, maintaining the remodeling of tissue comprises releasing second anchor 56 and anchoring it in place in the coronary sinus, as is shown in FIG. 5. In this exemplary embodiment, anchoring second anchor 56 comprises allowing second anchor 56 to self-expand, followed by an optional locking step to lock second anchor 56 in a locked configuration. Device 50 is then released from the delivery system, and the delivery system is removed from the patient.

Method steps that can be performed during the use and deployment of a tissue reshaping device according to the methods herein can be found in any of U.S. Pat. Nos. 6,976,995; 6,960,229; 7,351,260; 8,062,358; 7,311,729; 7,837,729; and U.S. Pub. No. 2006/0276891, all of which are incorporated by reference herein. Additional exemplary details of a tissue reshaping device that can be incorporated into device 50 can also be found in U.S. Pat. Nos. 6,976,995; 6,960,229; 7,351,260; 8,062,358; 7,311,729; 7,837,729; U.S. Pub. No. 2006/0276891.

In some embodiments, the remodeling to reduce leakage may take place during the procedure that implants the replacement valve, and in some cases the replacement mitral valve remains secured to its own delivery system until a sufficient degree of leakage reduction has occurred. The replacement valve may then be released from its own delivery system, and further monitoring for leakage may occur. Releasing the replacement valve may cause some slight movement with respect to the native valve, possibly causing some leakage to occur that did not exist prior to the release of the replacement valve. Monitoring for leakage and optional further remodeling can thus take place at any point during or after the replacement valve implantation procedure. The disclosure herein thus includes methods that can monitor and attempt to reduce leakage (including a further reduction in leakage) at any time during a replacement valve implantation procedure, of thereafter.

If, after the remodeling step (such as shown in FIG. 4), monitoring for paravalvular leakage reveals that paravalvular leakage has not been reduced by a desired amount, the method can further remodel coronary sinus tissue with the tissue reshaping device (or optionally with a different kind of tissue reshaping device if, for example, it is determined that a different type of device may reduce leakage better in a particular situation) to further remodel at least one of mitral valve annulus tissue, at least one native leaflet, and left atrium tissue in an attempt to reduce paravalvular leakage, and further monitoring paravalvular leakage.

The remodeling step, an example of which is shown in FIG. 4, may include plicating coronary sinus tissue with the tissue reshaping device. Plicating (or remodeling of another type) may occur before or after a second anchor (such as exemplary second anchor 56) is anchored in place, such as is described in U.S. Pat. No. 6,976,995, issued Dec. 20, 2005, which is incorporated by reference herein.

The manner in which the coronary sinus is remodeled may depend on the tissue reshaping device and/or the manner in which it is deployed.

In some embodiments, remodeling coronary sinus tissue with a tissue reshaping device comprises reducing the curvature of at least a portion of the coronary sinus. Exemplary methods of remodeling the coronary sinus that can reduce the curvature of at least a portion of the coronary sinus can be found in, for example, U.S. Pat. No. 6,976,995, which is incorporated by reference herein.

In some embodiments, remodeling coronary sinus tissue with the tissue reshaping device comprises increasing the curvature of at least a portion of the coronary sinus. Exemplary methods of remodeling the coronary sinus that can increase the curvature of at least a portion of the coronary sinus can be found in, for example, U.S. Pat. No. 6,569,198, which is incorporated by reference herein.

In some embodiments, remodeling coronary sinus tissue with the tissue reshaping device is at least partially caused by pulling on, or tensioning, the tissue reshaping device. Examples of tensioning a reshaping device can be found in, for example, U.S. Pat. No. 7,351,260, which is incorporated by reference herein.

In some embodiments, remodeling coronary sinus tissue with the tissue reshaping device is at least partially caused by straightening at least a portion of the tissue reshaping device. Examples of at least partially straightening device can be found in, for example, U.S. Pat. No. 6,976,995.

In some embodiments, remodeling coronary sinus tissue with the tissue reshaping device is at least partially caused by increasing the curvature of at least a portion of the tissue reshaping device, examples of which can be found in, at least, U.S. Pat. No. 7,351,260.

The act of delivering the tissue reshaping device to the coronary sinus can occur at any time relative to when the replacement valve is initially positioned within the native annulus. For example, the tissue reshaping device can be delivered to the coronary sinus before the replacement heart valve is delivered to the native annulus, after the replacement heart is initially expanded but before the replacement valve is released from a delivery system, or even after the replacement valve has been implanted and optionally released from a delivery system.

Device 50 shown in FIGS. 3-5 is merely an example of a tissue reshaping device that can be used to remodel tissue used in the methods herein to reduce paravalvular leakage. Other exemplary tissue remodeling devices and their methods of deployment that can be used to reduce paravalvular leakage can be found in the following references, all of which are incorporated by reference herein: U.S. Pat. Nos. 6,210,432; 6,402,781; 6,997,951; 7,192,442; 6,569,198; 7,192,443; 7,473,274; and U.S. Pub. No. 2003/0078465.

In some embodiments the methods can include monitoring for paravalvular leakage between an existing replacement heart valve and a second, or subsequently-delivered, replacement device configured to interface with the first replacement heart valve (optionally within the first replacement heart valve). That is, the methods herein can monitor for and reduce paravalvular leakage between two or more separate, non-native structures.

What is claimed is:

1. A method of reducing paravalvular leakage associated with a replacement mitral valve, comprising:
   in a patient in which a replacement mitral valve has been positioned proximate to a mitral valve annulus, intravascularly delivering a tissue reshaping device within a delivery device to a coronary sinus;
   deploying at least a portion of the tissue reshaping device in the coronary sinus from the delivery device; and
   applying a force to the tissue reshaping device to cause coronary sinus tissue to be remodeled and thereby remodel at least one of mitral valve annulus tissue, at least one mitral valve leaflet, or left atrial tissue,
   wherein remodeling at least one of mitral valve annulus tissue, at least one mitral valve leaflet, or left atrial tissue attempts to reduce paravalvular leakage around the replacement mitral valve.

2. The method of claim 1, wherein deploying at least a portion of the tissue reshaping device comprises allowing a distal anchor of the tissue reshaping device to expand within the coronary sinus.

3. The method of claim 2, wherein deploying at least a portion of the tissue reshaping device comprises allowing a proximal anchor of the tissue reshaping device to expand within the coronary sinus at a time subsequent to allowing the distal anchor to expand, the proximal anchor axially spaced and proximal to the distal anchor.

4. The method of claim 1, further comprising monitoring for paravalvular leakage around the replacement mitral valve at a time prior to deploying at least a portion of the tissue reshaping device.

5. The method of claim 4, further comprising performing a second monitoring for paravalvular leakage around the replacement mitral valve after remodeling at least one of mitral valve annulus tissue, at least one mitral valve leaflet, or left atrial tissue.

6. The method of claim 5, wherein if the second monitoring step indicates leakage has been reduced, maintaining the remodeling of the coronary sinus with the tissue reshaping device.

7. The method of claim 6, wherein maintaining the remodeling of the coronary sinus comprises allowing a proximal anchor of the tissue reshaping device to expand from the delivery device.

8. The method of claim 6, wherein maintaining the remodeling of the coronary sinus comprises locking an anchor of the tissue reshaping device in an expanded and locked configuration.

9. The method of claim 6, wherein if the second monitoring indicates leakage has been reduced, releasing the tissue reshaping device from the delivery device.

10. The method of claim 5, wherein if the second monitoring indicates leakage has been not reduced, applying additional force to the tissue reshaping device in an attempt to further reduce paravalvular leakage around the replacement mitral valve.

11. The method of claim 1, wherein applying a force to the tissue reshaping device comprises applying a proximally directed pulling force on the tissue reshaping device.

12. The method of claim 11, wherein the proximally directed pulling force is applied at a time subsequent to anchoring a distal anchor of the tissue reshaping device in the coronary sinus.

13. The method of claim 1, further comprising releasing the replacement mitral valve from a valve delivery device and thereby implanting the replacement mitral valve.

14. The method of claim 1, wherein remodeling coronary sinus tissue with the tissue reshaping device comprises reducing the curvature of at least a portion of the coronary sinus.

15. The method of claim 1, wherein remodeling coronary sinus tissue with the tissue reshaping device comprises increasing the curvature of at least a portion of the coronary sinus.

16. The method of claim 1, wherein remodeling coronary sinus tissue with the tissue reshaping device is at least partially caused by straightening at least a portion of the tissue reshaping device.

17. The method of claim 1, further comprising, at a time prior to the deploying step, expanding the replacement mitral valve into contact with one or more of left atrial tissue, mitral valve annulus tissue, native mitral valve leaflet tissue, or left ventricular tissue.

18. The method of claim 17, wherein the expanded replacement mitral valve remains secured to a replacement mitral valve delivery device when the deploying step is initiated.

\* \* \* \* \*